US006805677B2

(12) United States Patent
Simmons

(10) Patent No.: US 6,805,677 B2
(45) Date of Patent: Oct. 19, 2004

(54) WHEEL-LESS WALKING SUPPORT AND REHABILITATION DEVICE

(76) Inventor: John Castle Simmons, 7993 Cavershamwood La., Germantown, TN (US) 38138

( * ) Notice: Subject to any disclaimer, the term of this patent is extended or adjusted under 35 U.S.C. 154(b) by 0 days.

(21) Appl. No.: 09/960,293

(22) Filed: Sep. 20, 2001

(65) Prior Publication Data

US 2003/0191507 A1 Oct. 9, 2003

Related U.S. Application Data

(60) Provisional application No. 60/234,191, filed on Sep. 20, 2000.

(51) Int. Cl.[7] .................................................. A61B 5/00
(52) U.S. Cl. ....................................... 600/595; 700/245
(58) Field of Search ................. 600/595; 700/245–264; 340/825.19

(56) References Cited

U.S. PATENT DOCUMENTS 6,059,576 A * 5/2000 Brann ......................... 600/595
6,110,130 A * 8/2000 Kramer ....................... 600/595

* cited by examiner

Primary Examiner—Eric F. Winakur
Assistant Examiner—David J. McCrosky

(57) ABSTRACT

An apparatus and process for empowering those in wheelchairs and others with loss of limb control to walk, climb stairs, sit in ordinary chairs, use normal bathroom facilities and stand at normal height with their peers. It also provides a means to speed rehabilitation of the injured while providing superior physical therapy without draining professional resources. The apparatus is worn under normal clothing allowing them to also look normal.

33 Claims, 3 Drawing Sheets

WHEEL-LESS WALKING SUPPORT AND REHABILITATION DEVICE

Figure 1:
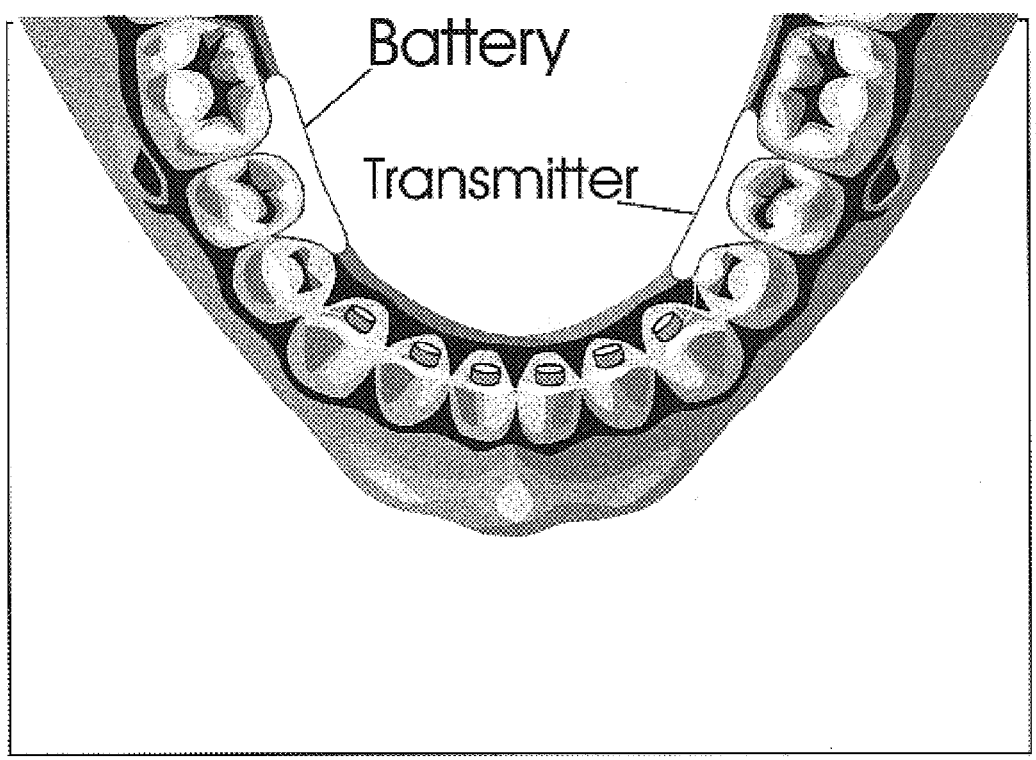
Figure 2:
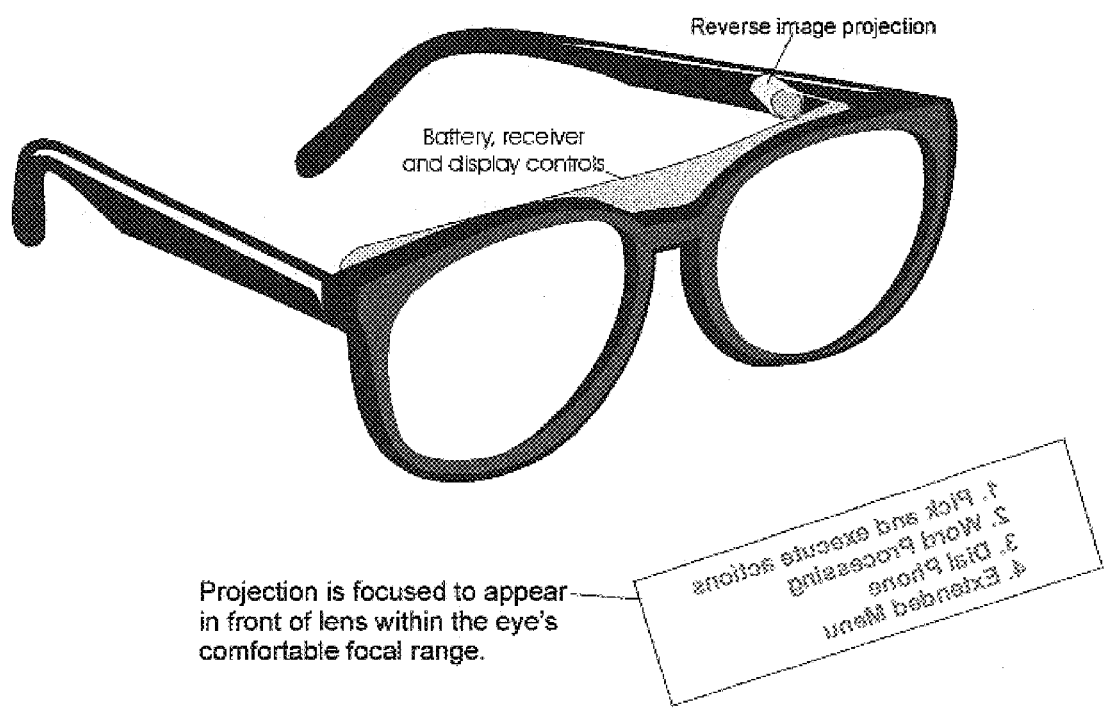
Figure 3:
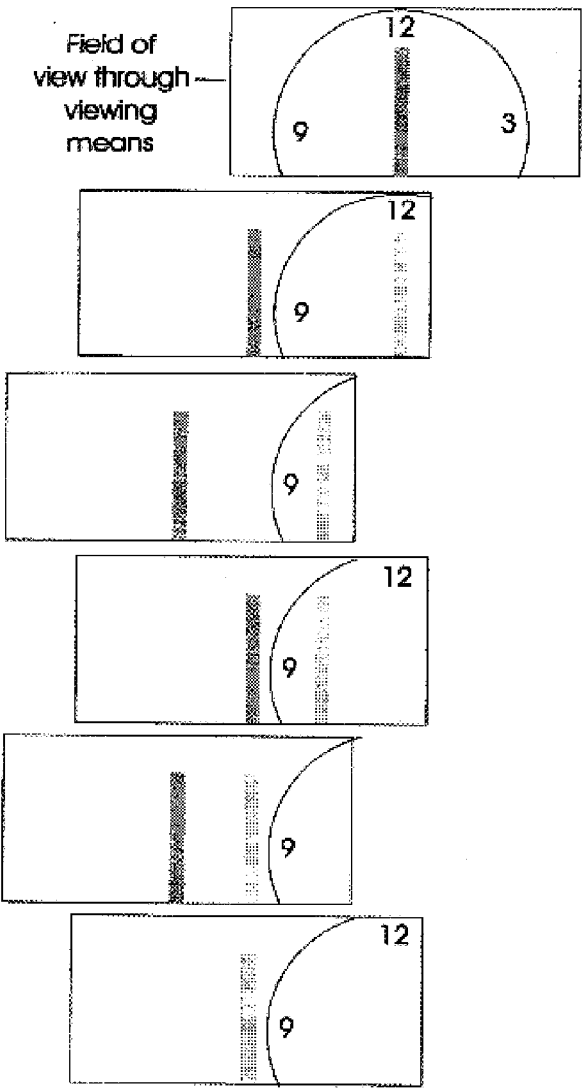

The present application claims the benefit of provisional application 60/234,191 which was filed on Sep. 20, 2000.

BACKGROUND OF THE INVENTION

Thousands of people struggle with crutches and wheelchairs all their life. There are new wheel based solutions that include balancing features but stairs, which have always been impossible, though climbable while balanced on wheels, can be very dangerous if the user is bumped or encounters a slippery or faulty surface and it isn't a smooth ride or an impressive entrance. Also, some paraplegics can only crudely control a powered wheelchair with their head or mouth movements and then only under almost ideal, smooth terrain circumstances and within a very limited scope of activities. For many, hands and feet are useless making them helpless dependents on others.

SUMMARY OF THE INVENTION

Using key elements of the disclosed invention, even these paraplegics can walk, climb stairs, hold a coffee cup, eat and drink. A visit to a hospital ward full of paraplegics is an effective gauge to see how impossible this has, up to now, seemed to the scientific and medical community.

This wheel-less, much more stable apparatus and process allows the user to get up out of a chair (or bed), stand up, walk on uneven terrain, climb stairs and appear, with ordinary street clothes, normal. It is a spin-off from other pending patents that resulted in the design of 1. lightweight, body worn equipment under normal clothing (but above a special layer) that controls and empowers the joints without bulky hydraulic levers,etc. (allowing the formerly disabled to look and move normally) and
2. unique software approaches (also a spin-off from another development) allowing precise and fluidly coordinated body control, with simple user direction of the new equipment.
3. an integrated balance control, user guidance and script process that allows the user to perform complex tasks in strange surroundings and on any terrain.

Even someone without control of their arms and legs can walk normally, look normal, open doors and, very importantly, stand normally at eye level with their peers. For many people, this is a complete solution eliminating the need for wheel chair ramps, wheel chairs, help in feeding or even special bathroom accommodations.

Additionally, the same 3 means provide a way for someone rehabilitating from an injury that has left them with little or no control or strength to be able to walk and work while protecting them from falling when their strength gives out suddenly. Gradually, over time, the amount of support and guidance provided by the system is decreased as the patient's strength and coordination return. However, the patient is under no circumstances allowed to fall. In addition to getting the patient up and walking quickly (speeding recovery, preventing lung and circulation diseases, while reducing atrophy and in-hospital time), it does so more safely and without the constant attention of medical personnel protecting them from injury. Also, much of the tedious physical therapy process of joint travel advancement therapy and muscle stretching can be done any time the patient desires, without burdening scarce medical personnel resources and without burdening special care facilities. There are many more benefits but I'm afraid I may have already put you to sleep.

This is accomplished in combination with the foundational patent "Natural Robot Control" and adds the above additional benefits.

The lightweight, date efficient and powerful and accurate joint control.

Consider a healthy person of similar build to the paraplegic wearing the same local user's equipment described above and cataloging certain operations from certain standard positions. As he gets up and moves around in the equipment, some things are done a little differently than above. Instead of the local processing means transmitting KCM's to the remote, these KCM'S stop short of transmission and are stored in local memory as steps, tiny timeslices of full body, simultaneous movements.

For example, from a standard, seated erect position (which itself becomes a static set of joint positions in a database table) the action cataloger leans forward and then stands up to a standard, erect standing position. Each change of the joint positions is recorded for each tiny slice of time throughout the operation in the processing means and recorded as an action (in this case we'll call it "StandingErectFromErectSeatedPosition"). In this sample embodiment, the data is stored in a relational database table. This is not the most compact database embodiment but it is the most easily understood. In many applications more compact forms such as traditional fixed length or delimited data formats with digital compression will be used. However, data is data and, for the sake of simplicity we use a familiar format for explanation here.

Extended Data Support Formats

The first table is named Actions.dbf and, contains the following fields.

ACTIONS.DBF:

| | |
|---|---|
| ActionName | Character field of 40 character length for the ease of documentation.<br>Example: "StandingErectFromErectSeatedPosition" |
| ActionType | 1 character alpha.<br>Examples:<br>A (for action). This type of record will have many related records in the Positions.dbf table described below. Each of those related records will be used to create multiple, sequential motions in tiny timeslices to achieve smooth motion as choreographed by the action cataloger.<br>P (for position). This type of record will typically only have one related record in the Positions.dbf table described below for each joint. That related record will store the precise angle and other optional information for each joint when the user is in the position described in the ActionName above. An example would be an ActionName of "PositionSeatedErect", an action type of P and a record in the Positions.dbf table below for the singular position and joint condition of each joint when the wearer of the local equipment is in that specific PositionSeatedErect position. There can be any number of such standard positions since their full attributes have been reduced to a simple database table. |
| ActionCode | A numeric field of 4 integer positions with a maximum of 9999 possible numbers<br>Example: 0001 |
| TimeSlice | A numeric field of 7 positions including 3 decimals (ex: 1234567 interpreted as 1234.567). 3 point decimal is assumed so the decimal point doesn't take up a database space. However, it is displayed in examples below with the decimal place for clarity. This is, essentially, the MDI. This determines the length of the timeslice in which we measure the movement of each joint. Naturally, the more rapid or intense the movement of the action being captured, the smaller the timeslice to provide fluidity in motion.<br>Example: 10.00000 (here in milliseconds this makes a timeslice $\frac{1}{100}^{th}$ of a second). It is |

-continued

ACTIONS.DBF:

possible to change this value during the execution of the action by adding a field to the positions.dbf table below and responding to it but that is not fleshed out in this sample embodiment. Of course, groups of actions could also be grouped together into a single by-reference Action allowing very long combinations of actions with a single "handle" or command.

There is a "1 to many" relationship between this table and the one below. That is, for each record in the table above, there can be many in the table below.

The second table is named Positions.dbf and contains the following fields:

POSITIONS.DBF:

| | |
|---|---|
| ActionCode | As above. This is the key field that relates the two databases. Each of the records in this table is related to a record in the above table based on this key field. |
| JointNumber | A numeric field of 3 integer positions. |
| SequenceNumber | A numeric field of 5 positions, all integer. Example: 00001 |
| NewPosition | A numeric field of 6 positions including 3 decimals (ex: 123456 which is interpreted as 123.456). Example: 179.801 or just under 180 degrees. Geometric degrees are used here for simplicity. In practice, applications engineers may instead use the equipment's minimum graduated position measure. |
| Pressure | (Optional.) A numeric field of 8 positions. In situations where carry payloads are substantial or sudden, athletic movement is required that would require a sudden change in pressure in excess of what the equipment would normally exert to achieve the position required in the timeslice allowed or in cases where the action is so delicate that less than the normal position acquisition pressure is required and to fine tune equipment for the special body characteristics of the end user, this field may be populated so that the equipment will immediately exert the appropriate force on this joint within each tiny timeslice. This value may be automatically calculated in a variety of ways. Values may be created programmatically based on joint specific experience based algorithms helpful to providing response. They may also be programmatically responsive to body worn sensors on the action cataloger, body weight and the rate of positional change between this and the preceding motion. Or, more simply and most powerfully (and as discussed in this sample embodiment) these values may be left blank when the action cataloger first creates the action sequence. Then, when the equipment is being worn by the ultimate user (in this example a paraplegic), the software will note when a joint does not achieve the desired position in the desired time or when it exceeds it or when the position is simply not achieved due to resistance and insert a programmatically calculated higher or lower pressure figure based on degree of shortfall/overkill to be used the next time. This experience based number will make it work better the next time. The next time the action is executed, it will tune itself even more finely to the limitations and special needs of the user. Thus the system will fine tune itself automatically to learn each action on each specific user and even adjust as they lose or gain weight or their mobility increases or decreases. |

It should be noted that the Positions table is also used to store other key data besides the above described applications.

EXAMPLES

1. Joint Angle Sensors. While joint angle can be measured by gear position or other actuator specific positional measure, it is advantageous in some applications to also have joint mounted angle position sensors to report back to the processor. For these applications, fields would have alternative values:
   a. Action Code: (same) Links this as something to be done along with other steps in this action.
   b. Joint Number: Here its a unique device number separate from the also numbered joint. The device, of course, is the sensor
   c. Sequence Number: (same) this keeps all forms of measurement in sync.
   d. New Position: Similar. This is the joint angle but as measured by the additional sensor.
   e. Pressure: (not used)
2. Pressure and Impact Sensors. For some applications numbered joint or limb pressure sensors are added. While pressure is known by the pressure controller as back pressure, increased speed and accuracy can both be accomplished by the addition of joint mounted pressure sensors.
   Alternative values are:
   a. Action Code: (same)
   b. Joint Number: Here its a unique pressure sensing device number separate from the also numbered joint. The device, of course, is the pressure sensor.
   c. Sequence Number: (same) this keeps all forms of measurement in sync.
   f. New Position: (not used)
   g. Pressure: Same but as measured by the additional device.
   Some pressure sensors aren't mounted on joints and some aren't as interested in pressure as in contact or the lack thereof. One example is the front and rear ball mounted pressure sensors on the sole of the foot. These record for each sequence number (timeslice) the pressure on that point on the sole of the foot. Another form of pressure related sensor is the "tickle"/minor impact sensors made optionally for any part of the body but particularly for the fingertips. All can store their data in each timeslice where they have activity in this format as and additional Position record.
3. Attitude Sensors: Pitch, roll, vector of motion and vector speed are important measures for balancing physically assisted users, remote robots (particularly when transmissions are slow and balance needs to be maintained between communications) and full motion support mechanisms (allowing somersaults, climbing stairs that don't exist except remotely, etc.) These are also useful for every change of their value that occurs in a timeslice of the action being processed.
   a. Action Code: (same)
   b. Joint Number: Here its a unique device number for the attitude sensor like 9991.
   c. Sequence Number: (same) this keeps all forms of measurement in sync.
   d. New Position: The first 3 characters are pitch degrees. The second 3 are Roll degrees. Example: 090359 for 90 degrees of pitch and 359 degrees of roll
   e. Pressure: The first 3 characters are for vector of motion and the other 5 are speed along that vector eg: 01000170 for 0010 degrees vector (yaw) which may always be measured as degrees of change in yaw since the last timeslice making mixing and matching of stored actions simpler. The 0017.0 (the decimal is implied) is the speed along the vector.

4. Distance Sensors: Body mounted distance sensors are also optionally worn to measure the anticipated distance to an object. When the distance sensor is foot mounted, this is extremely useful in anticipating a rock or hole in the road before contact is made by switching to a "high stepping" procedure from a normal walking procedure in progress or simply raising the foot until the distance meets or exceeds the recorded value. The sensors are also extremely useful, for example, in recording how far the glass that the action cataloger is picking up is from the hand at each timeslice. Then, if the user was a little too close when initiating the pickup the software can stop just a fraction of an inch prior to contact and allow the user to adjust with touches on the oral keyboard. More sophisticated software can actually use 3 triangulation aligned or 2 strategically aligned distance sensors to actually home in on the target once it is very close. Thus the distance sensors can actually make quickly grasping objects a smooth process and help navigate rough terrain.
   a. Action Code: (same)
   b. Joint Number: Here it's a unique device number for the distance sensor like 8880.
   c. Sequence Number: (same) this keeps all forms of measurement in sync.
   e. New Position: Distance to the object in this timeslice (driven by sequence number).
   e. Pressure: Used for advanced sensitivity measures. The first 4 characters are for relative velocity of the target and the last 4 is the acceptable range of error. The acceptable range of error can be programmatically defaulted or selected for an action as a whole by the action cataloger. Also, after the capture of the action data, the cataloger can fine tune the process by overriding the defaults where appropriate by manually entering tolerances. Also, tuning software can be developed simply to tune certain kinds of actions (like walking, stooping, sitting, etc.) by modifying these and other values after the action is initially captured.

5. Milemarker positions. Manually or programmatically entered milemarker positions are optionally added to record the exact position in the "stroke" of a repetitive recorded cyclical script as described further below. It allows the program to know, particularly when switching from one script to another mid-action, where to pick up in the new script. Regardless of how many joints and other devices are being monitored, there is typically only one milemarker record per sequence number in an action sequence (script).
   a. Action Code: (same)
   b. Joint Number: (1000 to identify this as a milemarker record)
   c. Sequence Number: (same) this keeps all forms of measurement in sync.
   f. New Position: (unused)
   e. Pressure: Used here to identify the percentage of progress towards the end of the stroke. Example 07701 interpreted with assumed 2 point decimal as 77.01 percent. The other 3 characters are available for other use.

6. Landing Zone Attitude. During action cataloging, the cataloging software calculates the attitude of the landing zone as described in "Landing Zone Precalculation" further below
   a. Action Code: (same)
   b. Joint Number: (1001 to identify this as a landing zone attitude record)
   c. Sequence Number: (same) this keeps all forms of measurement in sync. While there are only 2 of these per cycle in repetitive walking sequences, they must have a sequence number to be found and it can be the next available sequence number for the action at the point when the landing zone has been scanned by the foot sensors as described later.
   New Position: Used here to identify: Pitch.
      Example −020.01 for a negative pitch of 20.01 degrees
   e. Pressure: Used here to identify: Roll and Distance (from a central point in the scanned area).
      Example-1412073 for a negative roll of 141.2 degrees and 7.3 cm distance to the landing zone.

In an action cataloging session, the action cataloger could create a standard position by sitting in a common, frequently used standard position such as PositionSittingErect which is reduced to a single record in each table above. An assistant could create such a standard position by, first, filling in the fields of a record for the actions.dbf table. This could be done by any data entry means.

Example: First, create a standard, fixed position.

ACTIONS.DBF

| ActionName | ActionType | ActionCode | TimeSlice |
|---|---|---|---|
| PositionSittingErect | P | 100 | 20.000 |

Records: 1

The timeslice in milliseconds shown above effects a time for the operation of getting the user in this standard position of 3 seconds. Equipment responsiveness and the intensity of motion for the ActionName being catalogued will determine the appropriate TimeSlice and, for long sequences of tiny motion transactions, the TimeSlice will typically be much, much smaller. However, for the assumption of a standard position from who knows what kind of a position, a longer time is appropriate to prevent too much change occurring in too short of a time and thus potentially breaking the user's neck.

with this data keyed in, the action cataloger assumes a standard, erect, seated position. The following table is created as the processing means polls the position of the following joints. For the sake of simplicity we will consider only 3 joints performing this singular position assumption operation which results in 3 records in the Positions.dbf database table.

POSITIONS.DBF:

| ActionCode | JointNumber | Seq Number | NewPosition | Pressure |
|---|---|---|---|---|
| 71 | 34 | 1 | 179.000000 | |
| 71 | 41 | 1 | 014.000000 | |
| 71 | 77 | 1 | 300.000000 | |

They all have SequenceNumber 1 since they all simultaneously move to their assigned positions and there is only one step.

Of course, there are many more joints involved in standing up from a seated position. Still, for many operations, within a single slice of time, many joints will not change position and thus will have no record. Thus, as the database is being read and acted upon by the processing means, joints with no records for the sequence number being executed are not moved but their positions are maintained as they were. If, however, special pressure considerations are appropriate even when the joint angle is unchanged, a record will still be created for the sake of storing the appropriate pressure.

We now have created our first standard position named PositionSittingErect which, using the current invention's means, has reduced that full body position down to one record in the Actions.dbf table and one record for each joint in the Positions.dbf table.

Now, for example, we can create a catalogued procedure to move from such a standard seated position to a standing position. This, of course, can involve hundreds to thousands of steps for each active joint.

First, we create an Action.dbf record as above:

ACTIONS.DBF

| ActionName | ActionType | ActionCode | TimeSlice |
| --- | --- | --- | --- |
| StandingFromSittingErect | A | 100 | 20.000 |

Records: 1

Thus, for this operation, the console operator has decided that the minimum timeslice is 20 milliseconds or $\frac{1}{50}^{th}$ of a second.

With the actions.dbf record created for the StandingFromSittingErect action, the action cataloguer now, wearing the equipment, sits while the console operator selects the PositionSeatedErect position from a browse screen of Actions.dbf records and touches a keyboard key to signal execution of the procedure. Reading the Actions.dbf record and the Positions.dbf record just created earlier, the processing means using the means of the current invention as described above to assume the Positions.NewPosition positions recorded for each joint in the Positions.dbf table. The action cataloguer is thus, over a period of 3 seconds, gently moved into the exact position he was in when he created the standardized position even if the chair is somewhat different (since the joints are synchronized to form the body into the precise overall combination of joint positions with or without the exact same contours of the chair).

The console operator now selects from a menu "Capture Actions" and is prompted to select a record from the Actions.dbf table. The operator chooses the StandingFromSittingErect record just created and touches the Capture menu option.

From that point on until the operator selects "End Capture", 50 records per second (based on the TimeSlice selected of 20 milliseconds) are added to the Positions.dbf table for each joint that is active as the action cataloguer stands up. A sample is shown below but only considers 2 joints for a few of the many cycles. Since it takes about a second to stand up you would expect to have roughly 50 cycles and, thus, about 50 Positions.dbf records per active joint.

In the example Positions.dbf records below, there are 3 odd entries with G for JointNumber and numerical data in NewPosition and Pressure. As might be suspected, these are not joint angles or pressure information but attitude based balancing data. The NewPosition and Pressure numbers are actually attitude measures. In this example embodiment it is the information from a single main torso based sensor recording the erectness of the torso throughout the operation. As will be seen later, when differences from the recorded balance information are sensed by the user, this difference in numbers alerts the system to engage balance controls.

POSITIONS.DBF:

| ActionCode | JointNumber | SequenceNumber | NewPosition | Pressure |
| --- | --- | --- | --- | --- |
| 100 | 9991 | 1 | 002001 | 01000170 |
| 100 | 1 | 1 | 45.000 | |
| 100 | 2 | 1 | 14.000 | |
| 100 | 1 | 2 | 45.095 | |
| 100 | 2 | 2 | 14.001 | |
| 100 | 9991 | 2 | 359001 | 00900181 |
| 100 | 1 | 3 | 46.183 | |
| 100 | 2 | 3 | 14.012 | |
| . | | | | |
| . | | | | |
| 100 | 9991 | 50 | 001002 | 00800170 |
| 100 | 1 | 50 | 89.000 | |
| 100 | 2 | 50 | 20.000 | |

Assume the 9991 attitude sensor shown in this data is upper torso vertically mounted. While there was no significant change in roll recorded during the session (the action cataloger didn't lean to the left or right as he stood up) the pitch went quickly from a slightly leaning back 002 to a slightly leaning forward −1 degree (shown here as a positive 359 degrees). During the gap in the data where the dotted lines are the user attained a pitch of −30 degrees as he leaned forward but by the time the user was standing fully erect again (third line from the bottom) the pitch is an almost perfectly vertical 1 degree.

As can be seen, joint 1, roughly like a knee joint going from sitting to standing erect went from 45 degrees to 89 degrees over the duration of 50 twenty millisecond timeslices. Joint 2, on the other hand, was much less involved in the process and moved less than 6 degrees throughout the process. Joint 2 might have had only 10–15 records over the 50 cycles due to the occasional nature of its involvement.

The console operator selects "End Capture" and the record creation ceases. Using the processes above, the user could then create a standard position called StandingErect to capture the action cataloguer's now erect posture. From that point a new action sequence named StepWithRightFromStandingErect could be created to capture the action cataloguer's first step forward with his right foot in a walk to the point where the right foot is firmly planted and the left is beginning to come forward. Another could be created called OneFullStepSequenceFromRight that continues this motion, as acted out by the action cataloguer, back to the same point where he's on his firmly planted right foot with the left just beginning its forward swing again. It can be seen that a user, regardless of physical abilities, could now be caused to assume a standard seated position, stand up and then take any number of steps forward.

Of course, a single sequence standing and walking across the room, etc. could have been captured as a single sequence and, for many extended operations, this may be the best way. However, there is another new process that allows the user to choose his own actions interactively and fluidly based on a carefully broken down series of frequently used modular motions that can be strung together and summoned by the user himself.

One such new means is an orally controlled radio signal transmitter (FIG. 5) operatively connected to receiving means which is connected to the processing means described above such that the user could indicate the next modular operation to do or even key in a queue stored series of modular operations to be executed in a fluid sequence with the ability to change or reverse those instructions at any point. One embodiment of the oral keyboard is a series of tiny, sealed, push click switches attached to the back of each of several upper teeth (much like orthodontal brace anchors are glued on) just below the gum line where it can easily be clicked by touching it firmly with the tongue. See FIG. 5. Each such switch is connected to the other switches with mini ribbon connectors similarly anchored to teeth and, upon each close of any switch's circuit (when pressed by the tongue) it transmits via a miniaturized, battery powered transmitter a tiny, single frequency signal (each switch causes a different frequency or recognizable code) which is picked up by the sensitive receiver worn on the body just inches away from the transmitter. One wire in the ribbon serves as the antennae. The receiver, worn on the body, is operatively connected to the processing means also worn on the body such that the user can summon preplanned modules of motion as easily as the console operator did. Each transmitter switch's unique frequency, when received by the receiving means, is treated much like the depressing of a different keyboard key by the console operator by the processing means. Thus the user can "type".

A seated user could click an abbreviated sequence or macro of abbreviated sequences telling the apparatus to standardize his seated position, stand him up smoothly and begin walking forward until further notice (or to take x steps forward). This process could be interrupted by a user command (which, of course, like all these signals, could be oral to voice recognition means or by any other means the user has to interface to the processing means) to turn right, stop to a fixed standing position and/or start walking up stairs. Alternate walking sequences could include slowly veering right or left or all the way up to a hard right face.

The oral or other communications means could, in addition to "click" based commands, be continuous as needed commands. For example, the user could, while walking forward, continue to take steps as long as one key remained depressed. This "action until release" functionality is also useful in managing motion to appropriate fixed positions to accomplish more sophisticated processes like meeting and grasping a coffee cup. With that accomplished the user could easily assume a standardized "sipping posture" position and then, as a single standardized operation from a single command (based on that standardized position involving every joint in the body), bring the cup smoothly and precisely to his lips (precisely placed by neck, back, arm, etc. positions), tip the cup and sip the coffee at leisure.

Visual Interface (optional)

Allows the user to see the world around him while still monitoring his data. FIG. 6.

While an experienced user will not require a visual response (in practice, frequent motion controls must be memorized and executed fluidly for smooth, quick response action), a visual response option is another new development for the following reasons:

1. To allow the user to see what he's keyed in before executing it. He can see a scrolling list of the active command and those coming up below it as a means of checking and, if necessary, aborting an accidentally entered action. This speeds learning and adds safety.
2. To give visual aid to recall options and use fewer keystrokes because of context sensitive key codes displayed.
3. To allow the user who has no manual capacities to do extended functions from creating macro motion groups to writing letters, surfing the net or programming a computer.

This new development consists of ordinary looking glasses with a reverse image projected on the back (inside) of each eyepiece of the glasses with a focal plane calculated to be beyond the glasses and within the user's focal range so that the user can see (and see through the non-opaque projected image to see the world around him) the data that would ordinarily be on a computer screen. In this sample embodiment, the display is wide but short to minimize interference with the user's field of view even though the user can "see through" the reflected display.

Of course, mouse-like controls can be used using the "action until release" means described above along with clicking switches. This can be used for any number of user interfaces to allow quick operation with a minimum of clicks. The user could select letters from the screen or key in letters from key combinations. 6 switches are shown in the above example embodiment. If 5 are used for alpha data entry, only 2 clicks would be required per typical character as displayed on the screen. See sample below. Of course there are any number of other programmatic interface aids.

Sample screens:

Screen instructions
Touch 1 once to switch case, twice to toggle from numbers to characters or 3 times to leave this function
Currently in Alpha-Mode  Touch 21 for A, etc

| A | B | C | D | E | F | G | H | I | J | K | L | M | N | O | P | Q | R | S | T | U | V | W | X | Y | Z |
|---|---|---|---|---|---|---|---|---|---|---|---|---|---|---|---|---|---|---|---|---|---|---|---|---|---|
| 21 | 22 | 23 | 24 | 25 | 31 | 32 | 33 | 34 | 35 | 41 | 42 | 43 | 44 | 45 | 51 | 52 | 53 | 54 | 55 | 61 | 62 | 63 | 64 | 65 | 66 |

When the user touches 6 twice to switch to numerics the following screen toggles:

Numbers, etc.
For the number 1, touch 11, etc.

| 1 | 2 | 3 | 4 | 5 | 6 | 7 | 8 | 9 | 0 | , | . | " | / | + | - | ( | ) | * | @ | ! | # | & | # | = | $ |
|---|---|---|---|---|---|---|---|---|---|---|---|---|---|---|---|---|---|---|---|---|---|---|---|---|---|
| 21 | 22 | 23 | 24 | 25 | 31 | 32 | 33 | 34 | 35 | 41 | 42 | 43 | 44 | 45 | 51 | 52 | 53 | 54 | 55 | 61 | 62 | 63 | 64 | 65 | 66 |

Also 1 takes you to an additional menu, 11 back to Alpha Mode and 111 to leave this data entry function Visual response for user: Glasses.

Balancing Logic

In a perfect world, since the action cataloguer was in balance as he stood and walked across the room, the user following precisely the same motions should be in balance in smooth terrain. As long as the user stays at home or wherever surfaces are flat, things can work out well. However, people want to go wherever they want so, for those "out in the field" applications where floors aren't flat, etc., there are additional means. The attitude data stored in the example above records for each timeslice of each step the initial overall body attitude (and optionally many local body attitudes) and every change to it. To sense an out of balance condition is more difficult than it seems since many operations, like walking and running, require a temporary out of balance condition. There are existing balancing technologies of varying effectiveness (especially when dealing with legitimate and desirable out of balance conditions). Their failures are typically in allowing flexibility in terrain particularly as directed by a user "on-the-fly", i.e. in real time as the situations develop. In addition to attitude sampling and response systems that attempt to keep the element upright at all times, the current invention has the advantage of knowing at a full body level (including any or all limbs and the torso), at any point in time, what joint/limb should be where. Thus the current invention continually compares the current attitude readings with the original readings from the action cataloguer (who was "in balance" even when his body was, to an attitude sensor, out of balance) to sense an imbalance situation which could be caused by anything including the slightest slope in the road. This does not preclude the use of older balance sensing mechanisms being used in the current invention but does provide a superior means for recognizing and dealing appropriately with any exception condition quickly, before the user finds himself on his face.

There are several sensed indications that an out of balance condition exists or is coming soon from other unexpected conditions. Some of them are listed below.

Out of Balance or Adjustment Needed Sensing Means:
1. When any of the attitude sensors record a pitch, roll or yaw value inconsistent with the recorded value in the appropriate timeslice.
2. When an accelerometer on any part of the body records a different velocity along any of the pitch, roll or yaw vectors other than the one recorded for any frame.
3. When contact is made to a sole located, or otherwise located, pressure sensor when there is no pressure recorded at that time in the process (in that frame) such as stepping on a sudden rise in the terrain.
4. When contact is not made to a pressure sensor that should have been per the recorded session (such as stepping into an unexpected decline or a hole).
5. When an optional toe mounted and/or knee mounted (or other strategic location including the lower back to allow the user, for example, to sit down smoothly in chairs of different heights) sonar or other distance sensor senses the closest element in the path as being closer or further away than recorded acceptable distance. This could be, for example, a sudden incline, a rock or a hole.

There are a variety of ways to adjust balance once an out of balance condition is sensed or predicted. Contact and pressure sensors are useful for timing, comparison and calibration. However, though they are also useful in the current invention for balance adjustments and impact prevention/control, the advance detection means of the distance sensors for the purpose of impact prevention/control are given more attention in this description for their obvious advantages of advance reaction.

1. On the fly script switches

Scripts (action sequences from action.dbf and positions.dbf) can be switched "on-the-fly" (as the user is walking and at any point in the walking stride). Mid stride switches are made simpler by using a repetitive or "until further notice to the program" type action scripts. This script will continue to repeat itself in cycles until the user or the software (due to an exception) intervenes. The user can select, for example, a simple "four step" walking cycle (1.left foot down, 2.swing right, 3.right down, 4.swing left). Of course, there are actually hundreds of time slices (sequence numbers) in this process involving numerous joints throughout the entire body. Each of these timeslices relates to a frame (a group of positions recorded with the same action and sequence number in the positions table) which includes the all the attitudes, velocities, sonar distances and joint angle positions associated with that particular "snapshot" of time. There can be, for example, numerous scripts just for walking varying by speed, stride and slope arranged in a naturally transitioning order for easy "gearing up" for changing conditions. For example, the user may select a relaxed walking script for 0 slope (flat surface) with moderate speed and stride (the distance achieved with each step). This works fine until the slope of the terrain increases. The user then touches the up button to shift "up" to the next script which was recorded at a slightly greater slope. The program then picks up in the parallel frame for the new script.

There are several means for the program to identify the parallel frame in the new script so that a smooth transition between closely similar scripts is made. As is typical in emulations of real life, the methods, in practice, often work best in hybrids. Percentage of progress in the cycle is one means. If the cycles are catalogued in a smooth, fluid movement, the point 85 percent into the frames of the cycle of one walking script would be equivalent to the same position in the newly selected script. Another means is comparative joint angle or limb attitude. For example, the new script can pick up at the point where the angle of the front ankle tendon is the same as it was in the previous script. Or the new script could pick up at the point where the front active foot attitude is the same as the previous script. (The "active" foot is the one that is touching the ground or, if neither is touching, the one that will touch down next. However, when both feet are touching at the same time in a walking script, the last one to make contact is considered the active foot). Another means is the "mile marker" approach. Here, for frequently used cyclical scripts, action catalogers can even more finely tune shifts between scripts by entering a single mile marker record for each timeslice in the script to indicate the position in the full cycle stroke the time slice is in. Using the sample database structure as shown above, there would be, in addition to the other records in the Positions table, a single additional record for each timeslice identified as a timeslice record by its unique joint number (here used as a type identifier). The milemarker facility may seem useless when considering a smooth stroll of a walk. Everything is fluid and evenly spaced over time. However, the fine tuning of the milemarker can best be appreciated in scripts where sudden motions occur such that a more significant portions of the stroke are accomplished suddenly. For example, in a steep walking script on a decline (negative pitch), the action cataloger's smoothness is actually affected by gravity with changes in speed occurring at foot impact (a momentary slowdown) and muscle acceleration affects the smoothness of the stroke. Further, for very frequently used cyclical scripts like the walking series, it allows a very high degree of fine tuning as it allows adjustments to be made at a keyboard or programmatically based on how smoothly the transitions are made in practice runs.

Consider an example using a hybrid approach. As begun in the example above, the user selects a action walk script number 15 of 29 prepared action scripts arranged from 1 (steep decline) up to 15 (perfectly flat terrain) to 29 very steep. When the user senses an incline or his natural balancing senses tell him to "lean into" the incline, he can touch the up key once or a few times to skip up to a progressively steeper script (cataloged/recorded at a steeper incline). With practice, he can learn to do this as naturally as an able bodied person leans into an incline when his natural balancing senses tell him to do so.

This can adjustment to changing terrain can also be done completely automatically by sensing a need to adjust with distance sensors and scanned landing zone calculations shown in more detail under Intra-Script Balancing below.

To shift "gears" to the new script at an adequately parallel point in the stroke this example embodiment moves first to the most logical record based on percentage of stroke finished or milemarkers (if available, they are not required). Using, as promised, a hybrid approach in this example, the program then searches backwards and forwards a few records for the record that most accurately matches an index joint angle or limb attitude or both. For example, it can simply look for the record whose front of active foot pitch attitude measurement is closest to the current active foot pitch measurement (this is a better comparison value than the previous script's pitch value since it's more current) to minimize point of contact change in a single timeslice and to best respond to the current position of the user at the actual point of contact with the terrain.

With the gears thus shifted (i.e. now that we're following a script more reflective of the terrain), all the other joints of the body will move into more appropriate position for the terrain. In this case (increased incline), the user will be caused to lean forward more, incline the ankle joint to point the foot more upward and, in steeper incline scripts, bend the knees more. This will all be natural and coordinated since it is matching a script modeled by a person comfortably negotiating a similar incline. This can, of course, be done as much as is needed as a means of balancing. This switching of scripts can be manual or effected automatically which increases the smoothness of the transition by increasing the number of scripts in a family since the program can respond more quickly and often than a human user can do comfortably.

In addition to having a script series like the 1 to 29 series above, you can have parallel series with terrain or other adapting characteristics. For example, if the user were on script 21 of the basic walking series just discussed (on a significant incline) and a rougher terrain was observed by the user (when this is being controlled manually by the user) or when the sensors picked up close proximity impediments (where they were not in the script for automatic script switching applications) the switch could be made instantly to script 21 of a parallel "high grass stepping" series picking up at the same milemarker position in the new script. This allows single keystroke or automatically sensed and effected transitioning to an equally "full-bodied" script (appropriately directing all affected joints) that is tuned to the appropriate incline and also best adapted to the terrain.

This shifting from one cyclical script to another as a means of adjusting to the environment and maintaining a steady balance has a number of other advantages not the least of which is that this script also "knows" the various body attitudes associated with a stable condition. Thus, this script which is better attuned to the conditions is able to identify a problem and address it.

2. Intra-Script Balancing

In addition to the ability to switch scripts to adapt to incline and terrain, there are additional balancing controls that can operate within a script. These intra-script balancing processes, while not replacing other existing balancing techniques or those listed above or below, provide an understanding of an approach helpful in the applied use of the current invention.

The relationship of intra-script balancing procedures to on-the-fly script switches can be compared to a car's transmission. If you want to go 40 mph you need to get in, lets say, third gear. From here you fine tune the speed with the accelerator. You could go 40 mph in a lower gear perhaps by greatly exaggerating the accelerator (winding out the engine) but typically it's better to go ahead and shift. Intra-script balancing is comparable to the fine tuning of the accelerator while the on-the-fly script switches can be compared to the shifting of gears. After you "shift the gears" by changing to the appropriate script you have a range of adjustment within the script by adjusting joint angles to fine tune the balancing. While you could probably do with just intra-script balancing adjustments for many cases, for significant changes in terrain script switches provide full body adjustment to motion and terrain differences that affect the whole body and leave you with room for additional intra-script fine tuning balance adjustment as well.

Intra-script balancing can be effected manually by the user but can also be effected automatically.

Automatic intra-script adjustments can be based on sensed values that conflict with what should be expected based on the script such as an attitude in the current frame that conflicts significantly with the one recorded for that attitude sensor in that frame. Some categories of sensing adjustment needs are listed under "Out of Balance or Adjustment Needed Sensing Means" above. There is seemingly no limit to how complex you can make this process since any number of accelerometers, angle sensors, sonar sensors, etc. may be considered as part of and usable by the current invention. A limited process of the current invention is described below as monitoring and responding in a limited but effective manner.

The sensors can be placed anywhere and aimed at any angle but in this example are foot (special shoe) mounted. Not all of these listed are necessary but all are useful.

1. One or two (to better sense impediments) toe mounted distance sensor aimed at a relative pitch of 0 (straight ahead for a foot at rest on the ground).
2. One sensor on each side of the foot just behind the toes aimed at a relative pitch of −45, yaw 0 (forward and downward i.e. 45 degrees from the roll axis of the foot).
3. Two additional distance sensors placed near the heel on the side as close to a −90 degree pitch (i.e. perpendicular to the tangent to the earth when the foot is at rest and to the major roll axis of the foot) as the attachment means will comfortably allow. Placing one on each side of the heel allows a comparison distance to sense lateral inclines that would affect the roll stability of the user.
4. Another pair is placed near the heel at a pitch of −100 providing another valuable measure particularly as the heel comes down towards the terrain.
5. Front ball pressure sensors located on each sole just posterior to the toes registering contact with the walking surface as it returns the pressure value. One on each foot.

6. Heel pressure sensors located on the heel portion of each foot at terrain contact point.
7. Torso mounted attitude sensor located on the back of the lower side of the waist rotator so that it less affected by bends at the waist.
8. Foot mounted attitude sensors monitoring the pitch, roll and yaw of the length line of the foot (the roll axis) and the velocity of the foot along the measured vectors.

Any or all of these sensors can be used to capture information in scripts and capture it again as the script is executed so they can be compared and responded to appropriately. The current invention provides great latitude in the selection of and addition to the list of sensors above and the logic that responds to them.

For speed and data economy, these distance sensor records are recorded in the action cataloging process only when the distance sensed is less than a minimum value which (which can vary programmatically at different points in the cycle). Similarly, pressure sensors record (create cataloging records) only when actual pressure is registered. However, they are considered at all times during a user session to provide exception information whether or not anything is expected to be there to be measured.

Even within this category of intra-script balancing, there are several different and separable processes that can effect a better balancing control including:

Landing Zone Attitude and Distance PreScanning

The script in effect at the time just prior to planting the active foot could be the second (or $20^{th}$ for that matter) script in effect in this cycle alone as scripts can be switched at common mile markers within a cycle as a means of adapting to changing conditions in the potentially hundreds of frames in a single cyclical script. Typically action cataloging sequences will be recorded on very smooth terrain at specific pitches and, optionally, at varying combinations of pitches and rolls. However, roll exceptions can typically be controlled when executing a script recorded at 0 roll (as shown below) making the creation of special scripts at odd rolls unnecessary. Zero roll in recorded cyclical walking scripts is assumed here. This allows easy comparison to a stable norm for easy detection of and response to exceptions. As the inactive foot swings to prepare to become the active foot and begins to reverse its direction slightly and lower itself into the planted position, known software procedures can treat this as a scan of the foot planting area using distance sensors like those above thus providing a pre-landing pitch and roll value for the calculated landing plane for the foot. While all sensors (and others not listed here) can be used in especially deep algorithms to calculate landing zone distance from the foot's position, pitch and roll, adequate data from just 1 or 2 front mounted distance sensors along with the foot attitude sensors are both simple and adequate and will be considered here. Different applications and engineers will result in the use of many different means to use the current invention's sensing means to measure the landing zone plane. In this example we will create 2 virtual landing zone planes with one supporting the anterior ball joint area of the foot (this is the anterior landing plane) and the other supporting the heel area of the foot. Each of these sub-areas are broken into quadrants. The highest point in each quadrant is taken as the height of the quadrant and the triangle inscribed in space by the highest point in each of the highest 3 quadrants defines the landing zone sub-plane. Since the foot doesn't twist to accommodate differences in these 2 sub-plane plates, the pitch used is the average of the pitches for the 2 sub-planes (which can be thought of as a tangent to balance the foot upon) and the roll is the average of the 2 sub-plane roll values. However, as described in better detail elsewhere, for climbing steps and other conditions where the heel doesn't touch, only the anterior landing stub-plane is used to define the landing plane.

Multiple sensor arrays in excess of those listed above allow more points to be considered in the scan and can improve both speed (multiple sequential distance readings limits throughput) and accuracy. Also, while it is possible to scan ahead and read the frames ahead of the current position in a script to calculate at what point in the foot's preparatory to planting swing it is, in fact, "scanning" the foot planting area, in cyclical scripts this is unnecessary since the mile markers for this position in the swing where sensors are scanning the landing zone will already be known. In fact, when the action cataloger created the script (which can be modified at the keyboard later for extra fine tuning), values for landing zone pitch, roll and distance (on the aforesaid controlled terrain of appropriate attitude) can be saved as a single record with the appropriate sequence number reflecting the point (after the scan at cataloging) at which time it was calculated. There will, of course, be a record for each foot since a typical cycle includes both feet becoming the active foot. The landing zone plane, for the purpose of attitude scanning at least, is ordinarily based on the averaged values of the anterior landing plane and the posterior landing plane. However when, in the action cataloging process, there is a "square wave" change (significant change in distance while scanning from posterior landing zone to anterior landing zone such that long distances are experienced up to a point followed by sharply shorter distances after the recognizably square wave is encountered and the square wave occurs after passing the posterior landing zone), only the anterior landing sub-zone is used in the calculation of the landing zone attitude. This is particularly useful for climbing steps and very steep inclines where the action cataloger's heel never touches.

A fixed point in the landing zone, here the lateral center of the anterior portion of the front ball joint area (where the foot typically first encounters a step when climbing stairs or steep inclines), is measured for distance by averaging (since there are 2 sensors in sensor 2 in this example) the two distances at that point in the scan. Typically in a cyclical scan, this point in the scan will be a certain mile marker point (as it is in this example) but it can also be defined as a percentage point of completion of the stroke, a specific sequence number, etc. Thus, significantly before the user's foot is planted, the program can calculate the current pitch and roll of the upcoming landing zone, the distance to it and also look in the script to see the model pitch, roll and distance thus easily calculating the relative differences in pitch, roll and distance. This provides exceptionally useful values indicating exactly what adjustments need to be made before the foot hits the terrain.

Calculation Techniques

When the automatic monitoring software senses a significant difference in the recorded script value and the one being returned currently, calculations are executed which create adjustment variable values that endure for different periods based on which sensors initiate them. Adjustment variables created in response to foot based sensors like those above and the landing plane calculations can be maintained and included as part of the calculation (added to the frame demanded joint angle value) as long as the foot sensing the condition remains the active foot. This allows slower sensing equipment's responses to be effective over a number of frames. However faster equipment is increasingly inexpensive and compact and, as described in this simple example embodiment, it is very effective to do a complete recalculation of needed adjustments with each frame thus creating new adjustment variables to be used in the calculations for affected joints. Similarly, adjustment variables created in response to general body attitude sensors like the torso mounted attitude sensor in 7 and 8 are continually adjusted based on current reported general attitude values as they compare to recorded values.

Position Achievement Techniques

As shown in "Parallel Processing Embodiment" above (in the original patent), in each cycle of phases (each frame as applied to this application) and over multiple cycles the current invention can continually approach the desired position. The local user of the original patent is comparable to the user in this application. The recorded "correct" positions here are comparable to the original invention's remote data. In each application, the user equipment attempts to emulate the positions of the other dataset within controlled parameters. While it is not a necessary function, the back pressure resistance or some fraction of it can be applied to the user equipment as in the original patent to allow the user to bear at least a portion of the burden for computer aided therapeutic exercise, virtual reality training or entertainment. Those recorded values along with the adjustment variables adjust the way the user equipment follows the script by including these adjustment amounts in the calculation of the targeted positions for each joint. This process may be viewed such that in each frame the equipment achieves the desired positions before moving to the next frame. In fact, with adequately responsive equipment, this is a reality. This is especially realistic when considering that this application is favorable to the actuators being high-speed stepper motor based actuators (since emulation of position, not pressure is the key element). Still, to accommodate less responsive equipment or especially short frames (a frame is usually associated with a specific period of time referred to as a time slice) an approach not unlike that used for parallel processing in the original patent is optional. There, multiple intra-frame adjustments and, where necessary (when catching up in the next frame is necessary due to equipment slowness) inter-frame adjustments can be made as the equipment continually approaches the target. In the discussion of adjustments below, we will use the fully achieved angle within the frame period assumption.

Adjustments: Pitch

When a difference is sensed between the current landing zone for the currently active foot and the recorded landing zone (non-zero values for relative pitch, relative roll and relative distance), adjustment variables are created to temporarily adjust the attitude of the affected limbs to better accommodate the terrain. Great detail is not required here to disclose to an experienced person how to make these adjustments but, for example, if the relative pitch of the landing zone was positive 3 degrees (small enough to affect only the ankle/foot attitude), an adjustment variable would be created for the anterior ankle actuator such that, when it was added to the current frame demanded position, would result in an additional tendon retraction to achieve an additional ankle pitch of 3 degrees. Similarly, an adjustment variable would be created for the posterior ankle actuator to ensure that it extends additionally just enough to allow the 3 degrees of increased pitch. Thus, when the foot does impact the ground it encounters the ground with the foot attitude matching the attitude of the portion of the terrain it impacts consistent with the manner of contact intended (as modeled in the action cataloging process).

Adjustments: Landing Zone Height Higher Than Anticipated

While individual sensor data can be used for adjustments, the virtual landing zone is used here for it's ease of application. Landing zone recognized and distance sensor (like 2 and 4 above) recognized discrepancies between the current values and the script have similar adjustment responses. For example, if any of these sensors indicate that the landing zone surface plane as calculated above is higher than planned, adjustments can be made by one of the following means:

a. The script can be switched to a more "high steping" script intra cycle as shown above in On The Fly Script Switches.

b. The height of the foot can be adjusted (raised) by the amount of the difference by creating adjustment variables for the knee and hip joints which will result in the raising of the foot by that amount. The adjustment variables created will, however, as understood by all in those in the robotics industry, result in adjustments to not only the hip and knee but to the ankle as well to increase the height of the foot without changing it's attitude.

c. Both. The majority of the adjustment can be made by switching to the appropriate script with minor adjustments, if necessary, using adjustment variables Adjustments: Trip and Stub Preventions: Controls on the Currently Inactive Foot The above landing zone height adjustments do not protect the user from impediments just forward of the landing zone but through which the foot must pass in the normal stroke or from impediments to the foot during the positioning swing prior to (anterior to) the landing zone. Also, in the step climbing process, uneven steps require height adjustments (they require square wave responsive angle adjustments too but that is considered separately below). When, for example, sensor 1, which scans in advance of the positioning swing, returns a value closer than the value recorded for that sensor in the recording of the script for that frame (as it scans from frame to frame) or if it records any value at all when none was recorded in the frame, that indicates a possible trip or stub condition anterior to the landing zone. This is dealt with differently based on where it occurs.

Case A: If this obstruction exists in the landing zone itself. Nothing needed. It will be taken care of by the landing zone controls above.

Case B: If this is in the most anterior portion of the positioning swing, this mile marker or degree of completion identifiable position in the swing, while a very small portion of the swing, is vulnerable to kicking something even though it is outside (past) the landing zone. As soon as this condition is identified (and that can be made even earlier by adjusting the sensor angle if the equipment is too slow to respond) it's remedy can be begun immediately by one of several means including:

1. Switching to a script that purposely has no overswing for at least this cycle. (Incidentally, many walking scripts will have no overswing by their nature such as very steep inclines, steps and higher stepping scripts like those walking through high grass, etc.) Or 2. Negatively adjusting the frame demanded position of the knee and ankle. This can be done by creating adjustment variables that will be added (positively or negatively) to the values demanded by the frame. In this case it would create variables that would reduce the retraction value for the anterior knee tendon and increase the retraction value for the anterior knee tendon). Adjustment variables are also created for the ankle joint to maintain the foot's proper attitude while the knee's position is modified. These values would result in additional retraction of the anterior ankle tendon and the corresponding extension of the posterior ankle tendon. These adjustment variables will endure, and thus remain effective, until the frame identified by mile marker or degree of progress in which the foot would have normally already retreated behind the area now occupied by the impediment.

However, in the preferred embodiment of this option variable administered changes are implemented gradually as a percentage of the remaining distance to the point of calculated collision and then graduated to a return point. While there are many calculations that can effect a similar effect, the following is an example of one.

PD is the frame number in which the impediment was discovered.

FI is the frame number where the foot was scripted to pass the point currently occupied by the impediment.

MP (a frame number) is prior to FI as the foot swings forward by enough frames to be considered a margin of error. The foot will stop at a point prior to FI by the amount of travel scripted to have been covered by between MP and FI to allow a small distance between foot and impediment.

FR is the frame in the original script where the retreat from the overswing ends as the backwards motion of the foot is stopped by the heel planting on the terrain.

FM is the frame where the foot was scripted to reach its maximum forward extension.

$RP_{F,T}$ is the retraction position for tendon T in Frame F.

$NR_{F,T}$ is the newly calculated retraction amount for tendon T in frame F

At the time of discovery of the impediment, there are FM–PD frames in which to graduate the response. The advancement needs to be retarded to the joint positions in MP. At this point in the motion the affected joints are in a singular direction with no reversal of direction until just after FM. Now, the program wants to go through the same number of frames (and must to smoothly accommodate other body parts with scripted action in these frames) but arrive at a prior point, the point originally scripted for MP when actually executing frame FM. Thus, the positions of the anterior and posterior tendons for the hip, knee and ankle will be adjusted in frames PD+1 through FM proportionately. More specifically, these anterior tendons will have their change in retraction (from the previous frame) reduced and posterior tendons will have their retraction increased. One formula to accomplish this is below:

For any affected (hip, knee and ankle) tendon T in frame F (which is, by definition, between PD and FM) the new retraction amount for the tendon T is:

$$NR_{F,T} = (RP_{F,T} - RP_{F-1,T}) \times ((RP_{MP,T} - RP_{PD,T})/(RP_{FM,T} - RP_{PD,T}))$$

i.e. the New Retraction for a given tendon T in a given frame F (between PD and FM) is:
the change in retraction in this frame as compared to the previous frame ($RP_{F,T} - RP_{F-1,T}$) times
the relative originally scheduled change of MP–PD divided by the originally scheduled relative change of FM–PD).

Thus the forward portion of the swing is smoothly terminated just prior to encountering the impediment. However, there is another set of calculations and operations required since the script includes subsequent frames that reverse the path of the foot until it encounters the ground solidly. Actually, many scripts will not have an overswing that exceeds the landing zone but those don't need to be considered here. This description is specifically for those scripts that do include an overswing. The equation above provided the calculation of adjustment variables that caused the forward swing to terminate at MP, just prior to the impediment. However, if it is allowed to continue in a backwards direction between FM and FR as far as it was originally scripted to move between FM and FR, the foot would move too far backwards and miss part of the landing zone. Thus, for the frames FM+1 to FR, the following equation can be used to proportionately reduce the travel such that the foot terminates on the landing zone as it was originally scripted to. The new retraction amount for a tendon T in a frame F during the execution of frames FM+1 to FR will be:

$$NR_{F,T} = (RP_{F,T} - RP_{F-1,T}) \times ((RP_{MP,T} - RP_{FR,T})/(RP_{FM,T} - RP_{FR,T}))$$

Thus the foot never quite reaches the impediment and, in fact, does just what any normal walking person would do when encountering such an impediment just beyond his landing plane i.e. avoid the overswing of the landing plane in the first place to avoid the impediment (except that the program never forgets to look out for it). The adjustment change variables have been mathematically directed to avoid the obstacle and return the foot to the proper location without destabilizing the user with sudden stops aid starts. All the math makes the switching scripts option look even better but, in practice, there is usually the need, even with script switching, for adjustments for terrain that falls between the characteristics of scripts and this process provides that control.

Case C. The impediment appears as scanned to be before the scan reaches the landing zone: Note that the length of the effective landing zone is calculable by scanning the script frames. If the user is climbing steps it will begin with the frame where the square wave first indicated the step and end with the location of the most anterior portion of the foot comes into contact.

Sub Case 1: There is a square wave (this is a step which is optionally verifiable by a) the script if the user is running a step script and b) using step recognition of the anterior scans (steps can be recognized ahead by the distance sensors as the swinging foot scans the area for up to several feet ahead of the user such that the program knows when the next stride will encounter a step) or c) a square wave was sensed in the current frame or d) all 3.

This is a step that is a little higher than anticipated. Thus the true landing zone is being identified incorrectly as an impediment. Raise the foot either by creating and managing adjustment variables, switching scripts for the rest of this cycle to a higher stepping script or both.

Sub Case 2: The impediment's height and position are such that they will not reach the arc created by the foot in the positioning swing. There is nothing to do since they will already be stepped over.

Sub Case 3: The impediment's height and position are such that they will reach and impede the arc created by the foot in the positioning swing. Raise the foot as above either by creating and managing adjustment variables, switching scripts for the rest of this cycle to a higher stepping script or both. If adjustment variables are used to raise the foot prior to encountering the obstacle, they should, ideally be managed as in Intra-Script Balancing described above i.e. the changes are graduated and reversed in a graduated manner after passing the impediment to return the foot to the correct attitude.

Adjustments: Landing Zone Height Lower Than Anticipated

Case D. Negative Impediments (depressions in the terrain):

When the landing zone is lower than anticipated

Also do lesser value where you switch to a less high stepping script if it has occurred for 1 or 2 previous cycles Assumed: Sensor 1 returns a closer value than recorded for the frame. Cases are numbered below:

Trend Watching Controls

In many cases above, the script may have been switched to accommodate terrain. This goes both ways as a smoother terrain with no impediments can automatically switch to a less high stepping script. This can be done either immediately when a new cycle recognizes a larger than needed clear area or the program can require that this condition continue for several cycles before switching back to a less forgiving low stepping script to reduce the number of changes.

Special provisions for climbing steps. When the sensors pick up a square wave indicating a step (which may optionally be programmatically verified by an action title beginning with the word "Step:"), the program can adjust foot position forward or backward based on the position of the square wave now as compared to the script. The position in the scanned landing plane of the original (model) square wave in the script can be calculated on the fly by reviewing the scan portion of the script. However, the script can also contain the location of the square wave in the action cataloging sequence in the action.dbf table which eliminates a calculation. Either way, if the currently measured square wave is x mm to the anterior of the recorded square wave, the foot will be moved x mm forward of the frame demanded position so that the edge of the step encounters the foot at the modeled position on the foot. Because alignment with steps is rarely perfect and because steps often spiral, twin sensors on each side of the foot in the scanning process make it possible to observe a difference in angle of the line of the square wave. If the angle of the edge of the step (seen here as the angle of the square wave line assumed between the two points scanned by the twin sensors encountering the square wave) appears to have a relative yaw of −5 degrees, the program can either:

a. Effect an adjustment process (effecting an additional relative yaw of −5 on the ankle and then, once in firm contact with the step based on milemarkers and contact sensors and as soon as the other foot is Out of contact with the previous step, returning to the script's yaw. This has the effect of twisting the body supported by that foot in line with the step while returning the body to the script's positions. Or b. Switch to another script in the sequence for spiraling steps. These can be switched in and out seamlessly such that if the stairs spiral at a continuing subtraction of yaw of 7 degrees and the action cataloger only created scripts for 5 and 10 degrees, the two scripts can be alternated in a closest match process to achieve the desired effect. Or c. Both. This allows better full body modeling and flexibility as well as fine tuned adjustments within the scripts.

3. Both 1 and 2

As alluded to in both 1 and 2 above, it is frequently advantageous to use both. The script switch to get very close to the ideal script and the intra-script adjustments to fine tune.

Roll Adjustments. In a like manner, roll is controlled at the first level intra-script by adjusting the inside and outside ankle tendons to accommodate landing zone roll that differs from the current script. Script switches to a script with a roll closer to the current landing plane's roll, while not needed for most terrain and situations, is a useful means for dealing with extreme rolls that significantly effect the whole body. For example, if the user entered a roller derby on a highly banked track an appropriate script is the obvious choice.

Adjustments: Overall Body Balance

In addition to the controls described above, there are additional controls that can be applicable to the current invention. Those include the overall body balance and velocity controls. Though script switches would usually manage the bending of the waist to balance the body as inclines and even rolls change, an additional layer of control provides additional flexibility and security.

When switching of scripts to match terrain slope, etc. and even additional intra-script adjustments of the foot and lower leg still require additional control or when there doesn't happen to be a script that goes far enough for the particular situation at hand, an additional layer of control is provided intra-script.

It is possible for the foot to perfectly match the terrain and the full body script to be very close to perfect and there still be problems:

1. When close isn't close enough. It is possible that the script that best matches the conditions doesn't match it closely enough. This will result in conditions different from those recorded in the script. For example, when the attitude sensor on the back of the lower waist area returns pitch or roll values still differing from the script even though the landing zone met the foot perfectly and the script is in use is the best (because the next one "up" the list exceeds the adjustment needed). Then, based on the degree of variance from the scripted pitch and/or roll (with the response calculation based on well known procedures for calculating a graduated response not unlike calculations above), an excess pitch, for example, would be met with an increased retraction of the anterior waist tendon with a corresponding decrease of the retraction position of the posterior waist tendon causing the user to bend over enough to achieve the recorded attitude. In subsequent frames, subsequent adjustments as needed return the user to the proper attitude just as any normal person bends at the waist to balance. The head can also be tilted for additional balance but this is unnecessary for most applications. Roll differences still existing after other adjustments have been made below the waist (or when they are not being used as a user or developer option) would be similarly managed by adjusting the left and right waist tendons.

2. When something unexpected, such as being bumped by an external force, strong wind, a crumbling of the surface beneath the foot, etc. places the user "out of balance". For example, when an exceptionally strong wind hits the user in the face tipping him back slightly. In this case, a velocity sensor, like the one on the back of the lower waist area, would register a velocity along the current motion vector significantly different from the one recorded in the script. As in 1 above, the system would either:

a. Switch to a more forward leaning script in the same family or b. Adjust the angle of the waist and even the head/neck causing the user to "lean into" the wind just as any normal person would.

c. Both.

3. When a script is not running but a position needs to be maintained. For example, when no walking or other motion scripts are being executed but a standing (or even a sitting) position is being maintained. With no such adjustments it is perfectly possible for even a sitting person to fall over. Here the positions being maintained become the "persistent script" and any deviation from them is controlled by intra-script adjustments. These adjustments can be limited to the waist as in this example but can also include the head, hips, legs and ankles, etc.

Other User Directing Controls and Support Utilities

1. Head and/or eye directed yaw, pitch and roll directions. Many paraplegics have the ability to control the head and neck. This can be used to allow them to direct their path, maintain balance "manually", adjust interactively when eating and drinking and even adjust speed of any operation.

a. Direction: Yaw. User Self Guiding: The user can select at the keyboard to manually guide the yaw of the path he takes or manual can be set as the default condition. When active, the rotation of the head (or in other sample embodiments the movements of the eye or other controlling means that can be reliably sensed) can be used to modify the direction of travel. Ordinary magnetic or gyro based (or other) attitude sensors worn as part of the glasses or other head based mounting report a change in yaw since the last frame was executed. For example, it may have increased in yaw 1 degree relative to the previous yaw. The system is thus being instructed to move towards this new yaw position starting with the next change in active foot. Adjustment variables can be programmatically set, as described above, to adjust the yaw of the leg (controlled in this example embodiment by the rotator ring on each leg) on subsequent steps, or a turning script (a script that was cataloged with the user walking along a path that would, if more than 1 stride cycle was recorded which is not typical of repetitive scripts, eventually become a circle) can be switched to (which has the additional advantage of broad, general body adjustments which is especially effective when the magnitude of the adjustment is large. Selecting a turning script of a certain turning magnitude and switching back to a straight script when a turn is no longer needed allows for small or great adjustments) or both. More precision is available and fewer scripts are required when the two are used together.

b. Balance: Pitch and Roll User Controls. The above described balancing controls and others can, in addition to manual, automatic and script directed responses already discussed, be directed by the pitch and roll of the user's head, eyes or other direction means. In this example, the head is used. This can allow the user to maintain his own balance or override the autopilot controls described above by tilting his head in the direction he wants to lean. When eating at a table, this same control could allow him to automatically and proportionally lean forward at the waist as he tilts his head forward to better adjust the location of the head to meet a glass of water being raised to his lips using a drinking glass script. In fact, by matching the pitch and roll of the body to the relative pitch and roll of the head, as measured by attitude sensors and accelerometers optionally compared with fixed sensors below the neck or contact motion sensing devices, the user is not limited to motion in one direction but can lean forward and to the right, for example. Thus he can lean over and place his head precisely where he wants as the body flows in the same direction guided by the head which is what people do when they lean anyway. Also, since the arms move with the shoulders, guiding the upper torso with the head can fine tune where his hands actually contact a glass he's picking up in a drinking glass script, the pencil he's picking up (he could actually write with a pencil using a writing script that worked from text entered at the oral keyboard or by verbal command) in a writing script or a fork he's picking up, etc.

2. Step recognition. The image scanned by the foot sensors and/or other distance sensors can recognize the square waves of steps ahead. Other body mounted scanning sensors do augment the foot sensors.

a. Applied to distance-to-target automatic adjustments: This can be used to calculate the distance to the steps and adjust the walking script slightly so that the user doesn't have to make any manual positioning adjustments when he gets to the steps before switching to a step climbing script. That is important since the foot must be positioned properly before beginning a step climbing script. If the user was off by a half a step he would miss the step altogether and manual adjustments or "baby steps" to get into position for mounting steps is comparatively tedious.

b. Automatic switching to a step climbing script from a walking script and back: Step recognition can be used to determine just when to automatically switch to a step climbing script providing one element in an autopilot mode where the system is pointed (yaw directed) by the user and the rest is done automatically until the user intervenes with an adjustment tap on a key, changes a script or cancels the current script to make manual adjustments.

c. Automatic adjustment of tangent to line of step to be climbed: The program, recognizing the angle of the line of the square wave (by comparing the distance recorded by the left sensor and the right sensor on the square waved line) can automatically adjust yaw, using means like those described above, so that the user's yaw with respect to the step perfectly reflects the script's (which typically has the user perpendicular to the step).

3. Speed Control. While there are many means of communicating changes in speed to the program (including voice commands and "keyboard" commands), this example embodiment uses a tooth mounted pressure sensitive sensor that reports, using the same communication means as the oral keyboard, an increased speed command to the program with increased pressure and reducing it all the way down to a complete stop with reduced pressure. As the user directed pressure increases, the timeslice of the current frame of the current script is reduced proportionate to the amount of change in pressure. As the pressure is reduced, the timeslice effected is proportionately more. The script recorded timeslice is the standard against which the changes are calculated upon. When pressure approaches 0, the activity (which can vary from eating to walking) can stop altogether.

An equation sample effecting such a change is:

$$D=RD/(P/C)$$

where D=actual duration of the current frame, RD=the recorded duration for this frame, P=pressure of the sensor or other acceleration communication means and C=a constant reflecting a pressure typically falling in the normal operating pressure range of the activity which is selected to effect a comfortable range of speeds. As the pressure increases, D decreases (making the motion faster). As pressure decreases, D becomes larger (slowing). When P=0, D becomes infinity and motion has thus slowed to a stop.

4. Visual Control Interface. Many of the functions are aided by good feedback on the visual response means.
   a. Yaw control response. The user can optionally view on the visual response means a vertical bar or other indicator of his current yaw. Initially, of course, this would typically appear in the center of the display. For illustration, consider the vertical bar to be blue. Then, as he turns his head in the current frame 2 degrees, for example, to the left to indicate another desired yaw, another vertical bar (yellow) on the display, which was formerly in line with the blue bar, moves on the display two degrees to the right of the blue bar reflecting to the user the current yaw of the body's current motion. The blue bar indicates the desired relative yaw while the yellow reflects the current actual yaw. As the head turned, the blue (desired direction) bar stayed in the same location on the screen (in the middle) but the head (and attached visual display) rotated. The next time the active foot is changed (or earlier if scripts or procedures are written to begin an adjustment on a foot already planted) as it will be automatically directed to, the the body's actual yaw is, for sake of example, 1 degree less than it was previously compared to before the head was turned. The yellow (actual body yaw) bar has moved on the display 1 degree to the left reflecting the actual change. The head, unless the user adjusted it (and we will for example say he has not yet responded), has moved with the body another degree of negative yaw (to a relative yaw of −3 compared to the original yaw but only −2 compared to the body's current yaw). Still, the user will, since his job is to guide with the blue bar, continue to "fix" the blue bar on his target and will thus correct the yaw of the head with a change in yaw of 1 degree leaving the blue bar at a relative yaw of −1 degree compared to the current yaw of the body (Just as a driver turning left naturally corrects the wheel after the desired turn has been accomplished rather than leaving the wheel turned to the left). One degree of the two degrees has been corrected. The other will be done in the next step. Of course, many degrees can be corrected in a single step but this illustrates the process with simple numbers and that, though most corrections will be adjusted in a single step, it is possible to take more than one step to correct to a head demanded yaw correction.
   b Pitch and Roll indicators.

The system optionally provides an additional visible bar in the display which is similar to the vertical yaw bar above except that it is horizontal, moves up and down as the head moves up and down and it thus manages pitch. Similarly, like on an airplane display, roll indicators can be added this reverse projection image display.

5. Automatic distance and angle adjustment: when steps are automatically recognized and approached or the user has manually selected a step script, the software will: Adjust the coming angle of encounter. It will measure the coming angle of encounter and adjust the angle (either by switching to a turning script or by creating adjustment variables that will be used within the present script to twist the foot slightly just before it is planted and, as soon as the alternate foot is disengaged, return the foot to it's script demanded yaw which, since the weight of the body is placed on that foot, will have the effect of rotating the body in the desired direction) or both. Thus the user will be automatically perpendicular to the steps when he encounters them.
   b. Adjust the distance to steps (or a single step like a curb) automatically. It will use the adjustment within a script using adjustment variables means as described herein or select a walking script with gait length appropriate for the distance.

Thus when the user comes to the steps he is at the right angle and distance to begin ascending them with no manual intervention or delay. On the fly angle adjustment: The user can touch a tooth or other key to adjust the yaw of his walk a few degrees left or right in the current walking script 6. On the fly stride adjustment. Using the adjustment means described above to achieve his requests, the user can request by keyboard, voice or any other means (the user can use these or any other desirable means of interacting with the program for this or any desired activity) to nudge down or up the stride a bit.

Although there are numerous approaches (most of which are not part of the uniqueness of the current invention), an sequential approach beginning at where the rubber meets the road (the "shoes") is described here. ANKLE WORKS ALONE AS BEST IT CAN TO DO ADJUSTMENTS i.e. adding to or subtracting from the script's position to return the lower leg's attitude to the attitude stored in the script for that leg. But it only modifies it while the foot is in contact with ground. As soon as the foot leaves the ground, the ankle returns to the script's positions. There are also additional controls that can be effected at the ankle. If the user places the heel of a foot on level ground but the front ball (by the toe) sensor doesn't touch ground as expected in the script because there is a slant down in the pavement, even though the lower leg is not yet out of it's desired position, the ankle will point the foot further down looking for ground just as a normal walker would do. This action was based on the front foot pressure sensor and can prevent the need for any further action from the sensor on the lower leg by keeping the lower leg where it belongs. Of course, if it contacts ground too quickly, it can point the foot (toe) upwards at the ankle to prevent stubbing the toe and possibly tripping.

However, if the change in incline or terrain as sensed either by the sole pressure sensors (as compared to the script) or the lower leg attitude sensors, is beyond the ability of the ankle tendons to adjust, the hip and upper body will be at a pitch and/or roll different from the script. And thus the hip worn, vertically mounted attitude sensor senses a change in directional vector speed, the waist tendons are, operating independently of the ankle controls, used to balance from the waist to return the area below the waist to the script's attitude.

Thus, when in a balance sensitive standing or walking activity, extended balancing code can be activated which controls motion at the waist. There are many complex means to manage balance including those involving programmatic controlled adjustments of multiple limbs. However, in this sample embodiment, to minimize interference with other preprogrammed limb actions, only the user's waist joint (which functions like the wrist joint above with 4 position offsetting tendons) adds to or subtracts from the scripted angles to respond to out of balance conditions sensed as described below. In the simplest embodiment, if the user was walking uphill causing an out of balance situation, as data is compared to the recorded relationship with the central focus of gravity or otherwise sensed, the waist would be bent slightly in excess of the recorded values for the waist until the appropriate attitude is attained. Naturally, these necessary balance adjustments based on experience in a controlled environment can be programmatically saved by simply saving amended angle data over the original setting in the Positions.dbf table record for that joint in that timeslice. Thus equipment can be tuned to the individual user. Either the actual angle used (as amended to keep balance) can be saved in the Positions.dbf table over the originally captured value or a calculated value (typically a middle ground) can be overwritten to gradually tune the system to the individual. In either case, this provides the facility to know immediately when an out of balance condition is a problem and to remain in balance when unexpected circumstances occur. It also tunes the Positions.dbf table to accommodate consistent user reticence that might hinder actions (requiring learned system adjustment) and when the user and action cataloger simply have different weight characteristics.

Applications to Physical Therapy

In addition to allowing the disabled to care for themselves and even travel, the same invention allows the user to go through extensive therapeutic routines without the aid of a physical therapist. Following action sequences as above, the user is taken through the most complex routine with precision. In this case, for fidelity of action, the action cataloguer could take the role of the disabled while a qualified therapist goes through the motions while every nuance of the full body condition including speed of motion and pressure is reduced to database tables. Over time, even in a relaxed sleep state, the user can retrain lost body mobility and release actions.

Also, the same invention can provide a "safety net" allowing the user freedom to provide his own power (or some of it) while using balance controls and speed of motion caps to assure that he doesn't fall.

Applications also exist to teach batting, dancing, martial arts, etc. as the user "does it right" the first time every time as precisely as the expert acting as an action cataloguer did when the actions were captured in joint timeslice databases.

3D visual Interface

In this sample embodiment of the current invention, ordinary twin screen (one for each eye) "virtual reality" goggles or glasses can be used by local user controlling a remote. This provides an effective means of seeing what the 2 individual remote "eyes" (cameras) "see" in the image that is returned to the local user.

Also covered in a separate patent is a genuine three dimensional image viewed by the user of the precise scene encountered by the remote such that the user can focus his eyes not only on a general plane but can home in on any focal plane he desires providing a sharper image of the focal plan he's interested in and genuine depth perception as his own eyes focus individually down on a genuine three dimensional image.

3D Training: Simulation

An interesting wrinkle falls out of the combination of the 3D visual interface and the phantom sensory response of the invention. By recording both the action and the 3D image while performing brain surgery, the master surgeon could train any number of young doctors, even over the internet, as they see the 3 dimensional image of the brain and feel as their hand grasps the phantom scalpel, makes the cuts on the phantom brain before him and places micro-sutures.

Add the limitless motion option and a less gory but equally valuable ability that emerges is the ability to provide full surround 3D simulation of environments from airplane cockpits to an empty sky for a plummeting sky diver without the first prop, motion chair or hydraulic assembly—just wearing the suit and mounting the limitless control mechanism (FIG. 9).

But that is not what is claimed.

What is claimed is:

1. A limb control or assistance device comprising:
   a first reporting means for reporting joint dynamics of a first body; and
   a first computing means associated with the first body, operatively connected to first reporting means and equipped with a first memory means for storing the joint dynamics over time for one or more body parts as a body executes an action or series of actions, thus capturing the joint dynamics of one or many thus-learned actions or types of learned actions;
   a joint control means for controlling or modifying some or all of the joint dynamics of a second body;
   a second computing means associated with the second body, operatively connected to joint control means, and equipped with a second memory means for storing and recalling learned actions, to direct the joint control means to replicate or approximate these stored joint dynamics over a time period; and
   a learned action selection means, associated with the second computing means, for selecting a previously stored learned action to be replicated or approximated; wherein
   learned action selection means, whether in the form of a user directing the computing means to pick the next of any number of available learned actions, or in the form of a software-driven computer selection of the most currently appropriate of the learned actions, or any combination thereof, can direct the body through a series of potentially complex learned actions by selecting, as needed, learned actions which are then transitioned-to and replicated or approximated.

2. The device of claim 1 wherein joint dynamics comprise joint or body part position, angle, direction, force, contact pressure, speed, attitude, or acceleration, or any combination thereof.

3. The device of claim 1 wherein the first and second computing means, the first and second body, the first and second memory means, or any other elements capable of useful application to both the capture of a learned action or its replication or approximation, or any combination thereof, may be singular in that an element used at capture can also be used to perform similar or related tasks during replication or approximation; whereby
   instead of having redundant elements performing similar functions for the first and second body or even necessarily involving 2 different bodies, any portion of the same equipment elements, or body, or both may be used for both the modeling of a learned action and for its replication or approximation.

4. The device of claim 1 wherein the learned action selection means selects any number of learned actions to be used one after the other.

5. The device of claim 1 further comprising:
   a second reporting means for reporting the joint dynamics of the second body to enable the second computing means to automatically select, as necessary, the next learned action, wherein the second computing means, responsive to current data from the second reporting means, selects a learned action to replicate or approximate based on at least a portion of the preferred learned action's stored joint dynamics being a closer match to the congruent joint dynamics being currently reported by the second reporting means, or based on a recognized condition or set of conditions suggesting the choice of a specific or specific kind of learned action, or any combination thereof.

6. The device of claim 1 further comprising:
a user interface operatively connected to the second computing means, wherein a user guides the selection of learned actions of the learned action selection means in order to meet currently desired objectives or obstacles through the user interface.

7. The device of claim 1 wherein certain learned actions modeled and stored in the second computing means can be treated as cyclical and thus be repeated any number of times, wherein a potentially complex and repetitive activity can be executed cyclically for as long as desired.

8. The device of claim 1 wherein a learned action can be transitioned to from multiple points in a current learned action to a similar, or congruent or predetermined, or related, or any combination thereof, point in another learned action, wherein the learned action selection means can easily switch between learned actions as needed and can do so from potentially any point in the execution of a current learned action.

9. The device of claim 1 wherein a learned action can be transitioned to from multiple points in a current learned action to a point in another learned action that is chosen because its joint dynamics data, or other data stored with the learned action, or any combination thereof, at tat point in the learned action, is closest to or most favorable to the current actual joint dynamics or other sensor values.

10. The device of claim 1 wherein a learned action can be transitioned to from the current learned action to a point in another learned action using intermediate adjustments between the learned actions.

11. The device of claim 1 further comprising:
a user interface means associated with the second computing means for sending or adjusting instructions to the joint control means, wherein a user equipped with a pointing or other form of user interface device can direct the second computing means to send instructions to the joint control means to direct an action or, as the replication or approximation of a learned action is in progress, adjust the joint control instructions of the currently executing learned action, or any combination thereof.

12. The device of claim 1 wherein the second computing means, during the replication or approximation of a learned action, compares joint dynamics reported by a second reporting means to comparable stored joint dynamics for the current point in the current learned action and, when finding a difference that is beyond an established or calculated norm, or when the joint dynamics currently being reported from the second reporting means fit a recognizable pattern, or any combination thereof, responds by selecting and executing another learned action whose joint dynamics at some point are closer to or are a better match for the joint dynamics currently being reported, or by selecting another learned action known to be a solution for said recognizable pattern or norm, wherein second computing means may sense an undesirable, dangerous, destabilizing, or anticipated condition or any combination thereof and respond to it automatically.

13. The device of claim 1 wherein the second computing means, during the replication or approximation of a learned action, compares joint dynamics reported by a second reporting means to comparable stored joint dynamics for the current point in the current learned action and, when finding a difference beyond an established or calculated norm, or when the joint dynamics currently being reported from the second reporting means fit a recognizable pattern or characteristic, or any combination thereof, adjusts through commands to joint control means to correct.

14. The device of claim 1 wherein the second computing means, during the replication or approximation of a learned action, compares joint dynamics reported by a second reporting means to comparable stored joint dynamics for the current point in the current learned action and, when finding a difference, beyond an established or calculated norm, or when the joint dynamics currently being reported from the second reporting means fits a recognizable pattern or characteristic, or any combination thereof, responds by sending adjusted values to joint control means to offset or minimize differences, or by selecting another learned action, or any combination thereof, wherein second computing means can potentially recognize and respond appropriately to a condition much earlier by comparing these potentially large numbers of often interrelated factors and, potentially, vast amounts of elegantly synchronized multi-joint data allowing the recognition of an out of balance or other condition requiring adjustment before problematic momentums develop.

15. The device of claim 1 further comprising:
a first proximity sensing means operatively connected to the first computing means for measuring over time the proximity to an environmental presence, a distance in a direction to an object or potential impediment, or any combination thereof, from some point or points on or proximal to the body or body-worn equipment, during the capture of a learned action with the resulting data stored as part of or relatable to the learned action; and
a second proximity sensing means operatively connected to the second computing means for measuring proximity to any environmental presence, distance in a direction to an object or potential impediment, or any combination thereof from some point or points on or proximal to the body or body worn equipment, as a learned action is replicated or approximated for the purpose of comparison with the congruent or relatable proximity data stored with the learned action for recognition of differences indicating needed responses, wherein the second computing means may rapidly recognize and respond to an unanticipated placement of objects, terrain, or other environmental presences, or any combination thereof.

16. The device of claim 15 wherein as a learned action is being or is about to be replicated or approximated, computing means, responsive to a potential obstacle, which is sensed as a currently sensed distance response that is not found in the current learned action or is placed differently, either
adjusts the length of the stride of the current learned walking action or selects a learned walking action with a desirable stride length or other applicable stride factors so that the foot doesn't encounter the distance-sensed obstacle at an unfavorable point; or
goes around the obstacle by adjusting the current learned action's joint dynamics before sending them to the joint control means to modify the lateral direction or by accomplishing the same direction change by selecting a learned action that turns the body; or adjusts the height or placement of the foot or other body parts at points in the current learned walking action, or selects a learned walking action with a desirable clearance or other applicable factors, or any combination thereof.

17. A device according to claim 1 wherein a learned action or any series of learned actions are replicated or approximated to safely and precisely guide a living body though rehabilitation or other exercises.

18. A limb control or assistance device comprising:

a joint control means for the control of joint dynamics of a body wherein joint dynamics comprise joint or body part position, angle, direction, force, contact, pressure, speed, attitude, or acceleration, or any combination thereof;

a reporting means for reporting the joint dynamics of the parts of the body;

a computing means, operatively connected to said joint control means and said reporting means, equipped with memory means for storing the joint dynamics over time for one or multiple body parts simultaneously as a body models a learned action by performing an action or a series of actions, and for recalling those stored joint dynamics and directing the same or a similar joint control means on the same or another joint-control-means- equipped body to replicate those thus-learned actions over some time period; and a learned action adjustment means for adjusting joint dynamics through commands to joint control means, wherein learned action adjustment means, responsive to current conditions or objectives, whether the learned action adjustment means is computer software, or a user with a user interface, or any combination thereof, makes it possible to adjust the replication or approximation of a potentially complex learned action with potentially simple adjustments.

19. The device of claim 18 wherein:

for some or all of the equipment that is used both in learning a new learned action and for replicating or approximating it, one piece of equipment may be used for learning a learned action and another piece of equipment can serve the same or similar purpose as it is replicated or approximated.

20. The device of claim 18 wherein the computing means, or a user directing computing means through a user interface, or any combination thereof, may, in response to conditions or current objectives, select another learned action whereupon computing means transitions to and begins executing the newly selected learned action.

21. A method for assisting or directing in part or in full the mobilization of a body comprising, in any order, the steps of:

capturing joint dynamics data, where joint dynamics are defined as joint or body part position, angle, direction, force, contact, pressure, speed, attitude, or acceleration, or any combination thereof, while a learned action or multiple learned actions to be learned are modeled by a body being monitored for some or all of these values by sensors, storing data for each such learned action in retrievable form, placing a body in a joint-control means capable of controlling body part positions, selecting, by decision of computing means or by user selection through a user interface, or any combination thereof, the desired learned actions to recapitulate or approximate, using the data for each thus-selected learned action to direct the joint-control means to transition, when necessary, from current positions or any learned action already in progress, and replicate or approximate over time those stored values on affected body areas.

22. A method according to claim 21, further comprising:

directing changes to one or more instructions to the joint control means associated with a learned action responsive to a user interface, whereby the user can modify the body actions.

23. A method according to claim 21, further comprising the step of:

making offsetting, correcting, or other calculated adjustments through instructions to the joint control means responsive to current sensor readings when sensor values returned are different from comparable stored values or when the difference exceeds a tolerance.

24. A method according to claim 21, further comprising the steps of:

recognizing a needed adjustment to joint or body dynamics by comparing current data from one or more attitude sensors against congruent or comparable data that was captured and stored when the current learned action was modeled, to locate differences that are beyond a calculated or otherwise established value or that fit a pattern; and directing any needed error offsets or otherwise-calculated adjustments through commands to joint control means, or by transitioning to another learned behavior whose stored values are closer to or more ideal for the current sensor values, whereby a body is automatically balanced even when replicating or approximating a potentially complex learned action.

25. A method according to claim 21, further comprising the step of:

repeating a learned action in a cyclical manner.

26. A method according to claim 21, further comprising:

managing transitions from one learned action to another by selecting the point at which to leave the current learned action and the point in the next learned action at which to begin based on the two points being congruent or comparable in their respective sequences, or either of both of the points being predetermined as good transition points, or the points having similar or comparable joint dynamics, or any combination thereof.

27. A method according to claim 21, further comprising the steps of:

recording distances, or vectors, or both from body parts to objects or other environmental presences using sensors on or adequately proximal to the body during the capture of a learned action in a form relatable to points in the progress of the learned action:

sensing, as the learned action is replicated or approximated, using the same or other comparable sensors, the current distances or vectors or both between the body parts and objects or other environmental presences:

comparing congruent or comparable data elements to recognize unplanned presences, absences, or changes in location, or any combination thereon; and responding, when a difference or change exceeds a tolerance, by selecting and transitioning to a learned action whose stored values are closer to or more ideal for the current sensor values, or by adjustment commands to joint control means, or any combination thereof.

28. A method according to claim 21, further comprising the steps of:

identifying, by a computer program, or a user interface means, or by any combination thereof, a currently desired direction of travel as a learned action is being or is about to be replicated or approximated, comparing current sensor values for distance, or direction, or any combination thereof, from a plurality of body parts to objects or other environmental presences, against congruent or comparable sensor values that were captured as the behavior was being modeled, and responding by transitioning as necessary to a learned action, or by adjusting the joint dynamics through commands to the joint control means, or by any combination thereof, to bring the current joint dynamics closer to or more ideal for some or all of the learned behavior data and the desired direction whereby;

unanticipated objects or terrain may be automatically accommodated.

29. A method according to claim 21 further comprising the steps of:

recording distances, or vectors, or both from body parts to objects or other environmental presences using sensors on or adequately proximal to the body during the capture of a learned action, sensing, as the learned action is replicated, using the same or other comparable sensors, the current distances or vectors or both between the body parts and objects or other environmental presences, comparing congruent or comparable data elements in the recorded and currently-sensed data to recognize unplanned presences, absences, or changes in location, or any combination thereof, and responding by transitioning as necessary to a learned action, or by adjusting the joint dynamics through commands to the joint control means, or by any combination thereof, to modify the length of a walking stride, or the height or placement of the foot or other body parts, or the direction of travel, or other body part direction or placement, or any combination thereof, wherein the body favorably addresses or avoids altogether an unanticipated presence.

30. A method according to claim 21 further comprising the steps of:

gathering, during the execution of a learned action, a plurality of distance-to-the-nearest-object data from a plurality of distance sensors which effectively sweep or scan an area, locating, in the matrix defined by the data, lines or patterns associated with the predictable and sharply retreating or squared-off distance pattern of a line associated with the top or edge of a step, curb or similar obstacle, or another recognizable scanned distance pattern associated with an object or obstacle, or any combination thereof, to identify the location and placement of an object or obstacle; and modifying the length of the stride, the body's direction with respect to the upcoming presence, foot elevation, other body part position characteristics, or any combination thereof, by adjusting some of the instructions to the joint-control apparatus, or by transitioning to another learned action, or any combination thereof, whereby the body is caused to address the step, curb, hole, or other potential obstacles in a position already conducive to a safe negotiation.

31. A method according to claim 21 further comprising the steps of:

capturing, while a learned behavior is being modeled, information from sensors relating to the distance, or direction, or both, from locations on the body to objects or other environmental presences;

storing this sensor data in a form relatable to points in the progress of the learned behavior;

comparing, as a learned behavior is being replicated or approximated, current sensor data with congruent or comparable stored sensor data; and modifying, when a difference exists or exceeds a tolerance, the position of the affected body part or parts so that the data from current distance sensors, direction sensors, or any combination thereof more closely match or are more ideal for the comparable stored sensor data, wherein the body can be automatically directed to interact more precisely with objects.

32. A method according to claim 21 further comprising the steps of:

modifying, during the replication or approximation of a learned action and assisted by a pointing device or other user interface, the movement or positioning of a body part wherein a user can guide a body part to a more precise or desirable location, or have it arrive at a position at a more ideal time, or any combination thereof.

33. A method according to claim 21 further comprising the steps of:

recognizing a potentially unstable body position by the user looking for potential problems and alerting computing means though a user interface, or by computing means comparing current sensor values with known or calculated norms for stability, or by comparing current sensor values with comparable or congruent sensor values captured when the learned behavior was modeled to recognize a significant difference, transitioning to a stabilizing position or learned action whereby a fall or other danger may be averted.

* * * * *